United States Patent [19]

Gatfield et al.

[11] Patent Number: 5,753,473
[45] Date of Patent: May 19, 1998

[54] PROCESS FOR THE PREPARATION OF TRANS-2, CIS-4-DECADIENOIC ACID ETHYL ESTER

[75] Inventors: Ian Gatfield; Günter Kindel, both of Höxter, Germany

[73] Assignee: Haarmann & Reimer GmbH, Holzminden, Germany

[21] Appl. No.: 723,707

[22] Filed: Sep. 30, 1996

[30] Foreign Application Priority Data

Oct. 6, 1995 [DE] Germany ............... 195 37 235.2

[51] Int. Cl.$^6$ ........................... C12P 7/62
[52] U.S. Cl. ...................... 435/135; 435/921
[58] Field of Search ................... 435/135, 921

[56] References Cited

U.S. PATENT DOCUMENTS

| | | | |
|---|---|---|---|
| 3,953,377 | 4/1976 | Naf | 512/56 |
| 4,668,439 | 5/1987 | Billenstein et al. | 554/167 |
| 5,561,057 | 10/1996 | Tram et al. | 435/280 |

FOREIGN PATENT DOCUMENTS

| | | |
|---|---|---|
| 24 39 059 A1 | 2/1975 | Germany. |
| 1419230 | 12/1975 | United Kingdom. |

OTHER PUBLICATIONS

Bestmann et al., Liebigs Ann. Chem., No. 2, 363–365 (1982).
Takeoka et al., J.Agric.Food.Chem., Bd. 40, No. 10, 1925–1929 (1992).
Aps. Abstract JP 08–154690 Iwasaki et al Jun. 18, 1996.
Aps. Abstract JP 03–292893 Sasamoto et al Dec. 24, 1991.
Derwent Abstract 75–16384 W/10 L. Givaudan & Cie DE 2435059 [Feb. 75].

*Primary Examiner*—Herbert J. Lilling
*Attorney, Agent, or Firm*—Sprung Kramer Schaefer & Briscoe

[57] ABSTRACT

Trans-2,cis-4-decadienoic acid ethyl ester can be prepared from Stillingia oil by enzymatic transesterification with lipase from *Candida antarctica* in the presence of ethanol.

3 Claims, No Drawings

PROCESS FOR THE PREPARATION OF TRANS-2, CIS-4-DECADIENOIC ACID ETHYL ESTER

The invention relates to a process for the preparation of trans-2,cis-4-decadienoic acid ethyl ester ("DDAE" in the following) from other esters of trans-2,cis-4-decadienoic acid ("DDA" in the following). The process allows the preparation of natural DDAE.

DDAE is a flavouring which is the character impact compound of Williams pears. It is obtained in its nature identical form by an expensive synthesis. The starting substance for this is cis-1-heptenyl bromide, which is converted into the corresponding lithium-copper complex and finally reacted with ethyl propionate to give the nature identical ethyl ester, which is described as green, fruity, juicy, typically pear. However, the DDAE prepared in this manner is not a natural substance in the context of food law and therefore also may not be called a natural aroma substance.

Stillingia oil is a plant fat which originates from the fruits of the tallow tree indigenous to China (*Stillingia sebifera* or *Sapium sepiferum, Euphorbiaceae*). In addition to about 7% by weight of palmitic acid and about 70% by weight of $C_{18}$-fatty acids (about 40% by weight of linolenic acid), it comprises about 5% of DDA in the form of glycerides.

DDAE can be obtained therefrom by base-catalysed transesterification with ethanol; however, this is not a natural process in the context of food law, with the result that the product obtained may not be called a natural aroma substance.

Our own attempts to obtain DDA from Stillingia oil under natural conditions initially failed. Thus, for example, we attempted to split the natural triglycerides by treatment with superheated steam. Such a high temperature must be used in this process (>200° C./5 hours, about 80 to 90% cleavage of the lipids) that the sensitive DDA is oxidized and/or polymerized (content according to GC <0.2% of decadienoic acid).

Our own attempts to liberate the DDA by hydrolysis of the ester bond using esterases and lipases either failed completely or gave very small yields of the desired acid. The esterases and lipases tested thus evidently had too low a specificity with respect to DDA.

Our own attempts to form the ethyl ester via an enzymatic transesterification by means of the usual lipases and esterases were also unsuccessful, probably because of their lack of specificity. For example, esterase 30,000 from *Mucor miehei* from Gist-Brocades is in general capable of transesterifying esters of saturated aliphatic carboxylic acids with good yields. In contrast, with Stillingia oil, a crude product having a DDAE content of less than 0.5% by weight resulted in the course of 8 days. Nevertheless, the glycerides of other fatty acids which are constituents of Stillingia oil are transesterified smoothly to give the corresponding ethyl esters.

Further attempts with lipase PS from Pseudomonas species (Amano) and lipase B from *Candida cylindracea* (Biocatalysts) were also unsuccessful. The two enzymes are otherwise extremely suitable for esterifications. The reaction of coconut fat with ethanol in the presence of lipase B, for example, quite clearly leads to the liberation of ethyl caprylate and ethyl caprate in good yields.

Further attempts with the lipases of *Pseudomonas fluorescens, Chromobacterium viscosum* and pancreatic lipase also failed.

Surprisingly, it has been found that lipase from *Candida antarctica* is capable of transesterifying the DDA glycerides of Stillingia oil in the presence of ethanol to give DDAE—and in particular in a good yield.

The lipase can be employed in the form of the microorganisms themselves, as an extract thereof or, preferably, as the free or immobilized enzyme. It can be obtained, for example, from the company Novo Nordisk A/S, DK-2880 Bagsvaard, Denmark under the name Novozym® 435. It is a triacylglycerol hydrolase (IUB No. 3.1.1.3, CAS No. 9001-62-1) with about 7000 propyl laurate units per gram (determination: 60° C./15 minutes, substrate: 1-propyl laurate).

Lipase B from *Candida antarctica* is preferred.

The rate of the reaction depends, inter alia, on the enzyme/substrate ratio. As can be seen from Table 4 of the examples, an almost complete conversion of the DDA glycerides into DDAE is obtained after 2 days with 20% by weight of enzyme, based on Stillingia oil. At lower enzyme/substrate ratios, the reaction takes correspondingly longer.

The rate of reaction depends on the temperature and is not substantially influenced by stoichiometric excesses of ethanol.

The lipase can be employed repeatedly for many cycles without the desired activity changing noticeably.

DDAE can be isolated well from the crude reaction mixture by distillation. The product obtained has a purity of more than 90% by weight and also comprises about 6% by weight of trans-2,cis-4,cis-7-decatrienoic acid ethyl ester; the resulting product exhibits a very similar flavour to nature identical DDAE. The decatrienoic acid ethyl ester is formed by transesterification of the decatrienoic acid glyceride contained in Stillingia oil.

The invention thus relates to a process for the preparation of DDAE by enzymatic transesterification of other esters of DDA with lipase from *Candida antarctica* in the presence of ethanol.

"Other esters" are chiefly understood as meaning the esters of DDA which occur in Stillingia oil and which chiefly contain glycerides.

Transesterification of natural DDA esters with natural ethanol gives natural DDAE.

The invention furthermore relates to trans-2,cis-4-decatrienoic acid ethyl ester obtained by enzymatic transesterification.

The transesterification according to the invention preferably takes place in the absence of water. Other solvents may be used especially if they are inert towards the enzymes, such as, for example, hexane. The transesterification according to the invention is preferably carried out at temperatures between 20° and 60° C.

The reaction time depends on the amount used and the activity of the esterase and is about 24 to 72 hours. However, it may be advantageous to interrupt the reaction even earlier, for example after 12 to 18 hours, when the conversion is about 3 to 4% and to employ the starting materials recovered again.

The lipase can be employed in the pure form or on a support, to which it is immobilised chemically or physically. Handling of the immobilised enzyme is considerably easier. The amount of immobilised enzyme is 10 to 30% by weight, preferably about 20% by weight, based on the Stillingia oil.

When the reaction has ended, the lipase can be separated off by suitable measures, such as filtration or decanting, and employed again several times without a detectable loss in activity.

The following examples illustrate the invention.

EXAMPLES

The percentage contents in the following tables are based on the crude product obtained by distillation or filtration.

The data were determined via the areas under the gas chromatogram curves.

EXAMPLE 1 (COMPARISON)

A mixture of Stillingia oil (10 g), natural ethanol (1 g) and enzyme (1 g) was shaken at 20° C. for 3 days. The enzymes used were:

1. Esterase 30.000 from *Mucor miehei* (Gist Brocades)
2. Lipase PS from Pseudomonas species (Amano)
3. Lipase B from *Candida cylindracea* (Biocatalysts)

TABLE 1

| Ethyl ester of | % DDAE | | |
|---|---|---|---|
|  | Enzyme 1 | Enzyme 2 | Enzyme 3 |
| trans-2,cis-4-decadienoic acid | 0.4 | 0.05 | 0.10 |
| linolenic acid | 65.8 | 57.5 | 65.2 |

The values for the ethyl ester of linolenic acid show that the enzymes used are entirely capable of effecting transesterification of the main fatty acid of Stillingia oil.

EXAMPLE 2

A mixture of Stillingia oil (10 g), natural ethanol (2 g) and enzyme (1 g) was shaken under nitrogen at 45° C. in a closed vessel. Samples were taken after 3 and 7 days and analysed by means of GC for the content of DDAE.

TABLE 2

|  | Lipase |  | trans-2,cis-4-decadienoic acid ethyl ester GC area % after | |
|---|---|---|---|---|
|  |  |  | 3 days | 7 days |
| 1 | SP 523 | (Novo) | 0.35 | 1.15 |
| 2 | SP 524 | (Novo) | 0.10 | 0.10 |
| 3 | SP 525 | (Novo) | 5.60 | 5.55 |
| 4 | *Candida cylindracea* | (Biocatalysts) | 0.15 | 0.10 |
| 5 | *Mucor miehei* | (Biocatalysts) | — | — |
| 6 | Pancreatin | (Biocatalysts) | — | — |
| 7 | *Pseudomonas fluorescens* | (Biocatalysts) | 0.20 | 0.45 |
| 8 | *Chromobacterium viscosum* | (Biocatalysts) | 0.05 | 0.05 |
| 9 | Novozym 435 | (Novo) | 6.50 | 8.00 |

This clearly shows that the ability to obtain DDAE from Stillingia oil by transesterification with lipases is the exception. Good yields are obtained only with SP 525 and Novozym 435. Novozym 435 is immobilized lipase B and SP 525 is free lipase B from *Candida antarctica*.

EXAMPLE 3

A mixture of Stillingia oil (100 g), natural ethanol (20 g) and Novozym 435 (20 g) was covered with a layer of nitrogen in a 500 ml conical flask and, after the flask had been closed, was shaken at a given temperature. Parallel trials were performed at different temperatures. The liberation of DDAE was determined quantitatively by means of gas chromatography (see Table 3).

TABLE 3

| Temperature °C. | Content of ethyl decadienoate in % after 3 days |
|---|---|
| 20 | 2.2 |
| 30 | 2.7 |
| 40 | 4.3 |
| 50 | 4.4 |
| 60 | 4.5 |

The experiment was repeated at 45° C. Samples were taken after 1, 2 and 3 days. Table 4 shows that the optimum incubation time under the given conditions is about 2 days.

TABLE 4

| Incubation time (days) | Content of ethyl decadienoate in % |
|---|---|
| 1 | 4.1 |
| 2 | 4.6 |
| 3 | 4.6 |

EXAMPLE 4

A mixture of Stillingia oil (100 g), natural ethanol (20 g) and Novozym 435 (10 g or 5 g) was covered with a layer of nitrogen in a 500 ml conical flask and the flask was closed and shaken at 45° C. The contents of ethyl decadienoate was quantified by means of GC—see Table 5.

TABLE 5

| Enzyme (g) | Incubation time (days) | Content of ethyl decadienoate % |
|---|---|---|
| 5 | 1 | 0.70 |
|  | 2 | 1.50 |
| 10 | 1 | 1.50 |
|  | 2 | 2.50 |
|  | 3 | 3.20 |
|  | 4 | 3.90 |
|  | 7 | 4.40 |
| 20* | 1 | 4.10 |
|  | 2 | 4.60 |

*from Example 3

EXAMPLE 5

A mixture of Stillingia oil (100 g), natural ethanol (20 g or 30 g or 40 g) and Novozym 435 (20 g) was covered with a layer of nitrogen in a 500 ml conical flask and the flask was closed and shaken at 45° C. Samples were taken and analysed quantitatively (see Table 6).

TABLE 6

| Ethanol (g) | Content of ethyl decadienoate % |
|---|---|
| 20 | 4.50 |
| 30 | 4.10 |
| 40 | 3.90 |

Taking into account the various degrees of dilution, it can be calculated that the efficiency of the formation of the ethyl ester in this range is independent of the ethanol concentration. Mathematically, the equimolar ratio is about 16 g of ethanol per 100 g of Stillingia oil.

EXAMPLE 6

A mixture of Stillingia oil (100 g), natural ethanol (20 g) and Novozym 435 (20 g) was covered with a layer of nitrogen in a 500 ml conical flask and the flask was closed and shaken at 45° C. After 2 and 3 days, the contents were filtered off, further Stillingia oil (100 g) and natural ethanol (20 g) were added to the immobilized enzyme, the mixture was covered with a layer of nitrogen and the flask was closed and shaken. A total of 12 cycles were run with the same enzyme without the enzymatic activity decreasing noticeably (see Table 7).

TABLE 7

| Cycle | Incubation time (days) | Content of ethyl decadienoate (%) |
|---|---|---|
| 1 | 1 | 4.5 |
| 2 | 1 | 4.2 |
| 3 | 1 | 4.2 |
| 4 | 2 | 4.6 |
| 5 | 2 | 4.2 |
| 6 | 2 | 4.3 |
| 7 | 2 | 4.5 |
| 8 | 3 | 4.4 |
| 9 | 3 | 4.0 |
| 10 | 1 | 4.1 |
| 11 | 1 | 4.2 |
| 12 | 3 | 4.8 |

EXAMPLE 7

About 500 g of the filtrate collected from Example 6, having a content of 4.3% by weight of ethyl decadienoate, were subjected to purification by distillation. The distillation was carried out such that a preliminary fraction of about 10% by weight of the amount employed was first isolated. This preliminary fraction had a content of ethyl decadienoate of about 40% by weight. Recovery of the ethyl decadienoate was about 95% at this point. This preliminary fraction was then subjected to fine distillation. Fractions which, according to GC, had a typical purity of DDAE of 93% or more were obtained. The product thus obtained tasted very clean and typically of Williams pears and was equivalent in taste to nature identical DDAE. The main impurity was the ethyl ester of trans-2,cis-4,cis-7-decatrienoic acid, at about 6%, which likewise occurs in Stillingia oil and is transesterified with the enzyme used.

EXAMPLE 8

A mixture of Stillingia oil (5 kg), natural ethanol (1.0 kg) and Novozym 435 (1.0 kg) was covered with a layer of nitrogen in a 20 l glass vessel and stirred slowly at 45° C. The vessel was provided with a water condenser in order to minimize losses of ethanol by evaporation. After an incubation time of in each case 2 to 3 days, the reaction was interrupted. Fresh Stillingia oil and natural ethanol were added to the enzyme which had been filtered off and stirring was continued. A total of 10 cycles were carried out, the content of DDAE from the individual filtrates varying between 4.0 and 4.7% by weight.

We claim:

1. Process for the preparation of trans-2,cis-4-decadienoic acid ethyl ester by enzymatic transesterification of other esters of trans-2,cis-4-decadienoic acid with lipase from *Candida antarctica* in the presence of ethanol.

2. Process according to claim 1, in which Stillingia oil is employed as the source of the other esters.

3. Process according to claim 1, in which the transesterification is carried out in the presence of natural ethanol.

* * * * *